United States Patent
Zhuang

(10) Patent No.: US 12,321,653 B2
(45) Date of Patent: Jun. 3, 2025

(54) CONTROL DEVICES AND METHODS FOR CONTROLLING IMAGE DISPLAY

(71) Applicant: SHANGHAI UNITED IMAGING HEALTHCARE CO., LTD., Shanghai (CN)

(72) Inventor: Weiran Zhuang, Shanghai (CN)

(73) Assignee: UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/338,283

(22) Filed: Jun. 20, 2023

(65) Prior Publication Data
US 2023/0409267 A1    Dec. 21, 2023

(30) Foreign Application Priority Data

Jun. 20, 2022   (CN) .......................... 202210723039.0

(51) Int. Cl.
*G06F 3/14* (2006.01)
*G06F 3/04845* (2022.01)
*G06F 3/0488* (2022.01)
*G16H 30/40* (2018.01)

(52) U.S. Cl.
CPC ............ *G06F 3/14* (2013.01); *G06F 3/04845* (2013.01); *G06F 3/0488* (2013.01); *G16H 30/40* (2018.01)

(58) Field of Classification Search
None
See application file for complete search history.

(56) References Cited

U.S. PATENT DOCUMENTS

| | | | | |
|---|---|---|---|---|
| 2003/0197724 A1* | 10/2003 | Reed | ..................... | G06F 3/0482 715/738 |
| 2007/0236475 A1* | 10/2007 | Wherry | ............... | G06F 3/04883 345/173 |
| 2008/0267588 A1 | 10/2008 | Iwase et al. | | |
| 2009/0083665 A1* | 3/2009 | Anttila | .................. | G06F 3/0482 715/834 |
| 2011/0055772 A1* | 3/2011 | Hatambeiki | ..... | H04N 21/42222 715/863 |

(Continued)

FOREIGN PATENT DOCUMENTS

| | | |
|---|---|---|
| CN | 102568514 A | 7/2012 |
| CN | 104254005 A | 12/2014 |

(Continued)

*Primary Examiner* — Andre L Matthews
(74) *Attorney, Agent, or Firm* — METIS IP LLC

(57) ABSTRACT

A control device used for controlling a display of a medical image sequence on a display device may be provided. The control device may include a touch control panel. The touch control panel may include a plurality of predetermined regions corresponding to a plurality of gesture instructions. The control device may be configured to receive a target gesture instruction with respect to a target predetermined region among the plurality of predetermined regions. In response to the target gesture instruction, the control device may be configured to generate a control signal for controlling the display device to perform a target operation on the medical image sequence based on a corresponding relationship between the plurality of gesture instructions and a plurality of operations of the display device.

18 Claims, 5 Drawing Sheets

100

↓ Pressing: displaying /stopping displaying images

↔ Toggling to left or right: switching images

↕ Toggling to up or down: switching image sequences

↻ Rotating: switching reference images

(56) References Cited

U.S. PATENT DOCUMENTS

| | | | | |
|---|---|---|---|---|
| 2013/0063384 | A1* | 3/2013 | Ito | G06F 3/0485 |
| | | | | 345/173 |
| 2016/0188181 | A1* | 6/2016 | Smith | G06F 3/04886 |
| | | | | 715/765 |
| 2017/0038926 | A1* | 2/2017 | Fram | G06F 1/1694 |
| 2019/0191208 | A1 | 6/2019 | Coenen et al. | |

FOREIGN PATENT DOCUMENTS

| | | |
|---|---|---|
| CN | 104735544 A | 6/2015 |
| CN | 104935991 A | 9/2015 |
| CN | 105957541 A | 9/2016 |
| CN | 106231343 A | 12/2016 |
| CN | 106507173 A | 3/2017 |
| CN | 110324717 A | 10/2019 |
| CN | 110460907 A | 11/2019 |
| CN | 110795648 A | 2/2020 |
| CN | 111061412 A | 4/2020 |
| CN | 112752138 A | 5/2021 |
| CN | 113542830 A | 10/2021 |
| CN | 113573144 A | 10/2021 |
| CN | 114637439 A | 6/2022 |
| JP | H09102027 A | 4/1997 |

* cited by examiner

100

↓ Pressing: displaying /stopping displaying images

↔ Toggling to left or right: switching images

↕ Toggling to up or down: switching image sequences

↻ Rotating: switching reference images

CONTROL DEVICES AND METHODS FOR CONTROLLING IMAGE DISPLAY

CROSS-REFERENCE TO RELATED APPLICATIONS

This application claims priority to Chinese Patent Application No. 202210723039.0, filed on Jun. 20, 2022, the contents of which are hereby incorporated by reference.

TECHNICAL FIELD

The present disclosure relates to medical imaging technology, and in particular, to a control device and a control method for controlling a display of a medical image sequence on a display device.

BACKGROUND

Medical imaging technology has been widely used in clinical examination, disease diagnosis or treatment in recent years. With the development of the medical imaging technology, a large number of medical images (e.g., multiple images of different sections of a subject, multiple images collected at different times, etc.) are obtained during a scan. In order to obtain accurate information from the medical images, a user (e.g., a doctor) needs to view a large number of medical images through a display device. The display of the medical images on the display device is controlled via a control device.

SUMMARY

According to an aspect of the present disclosure, a control device used for controlling a display of a medical image sequence on a display device may be provided. The control device may include a touch control panel. The touch control panel may include a plurality of predetermined regions corresponding to a plurality of gesture instructions. The control device may be configured to receive a target gesture instruction with respect to a target predetermined region among the plurality of predetermined regions. In response to the target gesture instruction, the control device may be configured to generate a control signal for controlling the display device to perform a target operation on the medical image sequence based on a corresponding relationship between the plurality of gesture instructions and a plurality of operations of the display device.

In some embodiments, the plurality of predetermined regions may include a quick browse region, a determination region, and a direction adjustment region, and the quick browse region may be located between the determination region and the direction adjustment region.

In some embodiments, the quick browse region may be a ring region around the determination region, and the direction adjustment region may include four sub-regions evenly spaced outside the quick browse region.

In some embodiments, the target predetermined region may be the direction adjustment region. The target gesture instruction may include a press operation on the direction adjustment region. The target operation may include at least one of switching images in the medical image sequence, switching the medical image sequence to display another medical image sequence, or moving a cursor on the display device.

In some embodiments, the target predetermined region may be the determination region. The target gesture instruction may include a press operation on the determination region. The target operation may include at least one of displaying the medical image sequence, stopping displaying the medical image sequence, or choosing an image in the medical image sequence.

In some embodiments, the target predetermined region may be the quick browse region. The target gesture instruction may include a sliding operation on the quick browse region. The target operation may include changing a switching manner of images in the medical image sequence.

In some embodiments, the target predetermined region may be any region of the touch control panel. The target gesture instruction may include a single direction sliding operation on the region or a dual direction sliding operation on the region. The target operation may include at least one of moving a portion of an image displayed on the display device, enlarging an image displayed on the display device, or shrinking an image displayed on the display device.

In some embodiments, images in the medical image sequence may be displayed on the display device with an initial play speed. The target operation may include adjusting the initial play speed of the medical image sequence by an adjustment value. The initial play speed may be determined based at least in part on feature information of the medical image sequence.

In some embodiments, the control device further may include a speed adjusting element. The target gesture instruction may include a press operation on the speed adjustment element. The adjustment value may be determined based on the press operation on the speed adjusting element.

In some embodiments, the speed adjusting element may include a pressure sensor. The adjustment value may be determined based on a pressure exerted on the pressure sensor by the press operation.

In some embodiments, the initial play speed and the adjustment value may be selected from one or more groups of reference speed parameters each of which may include a reference initial play speed and a reference adjustment value based at least in part on the feature information of the medical image sequence.

In some embodiments, the adjustment value may be determined based on one or more historical gesture instructions received by the touch control panel in a preset historical period.

In some embodiments, the control device further may include an identification component configured to collect identity information of a user that operates the control device.

According to another aspect of the present disclosure, a medical system may be provided. The medical system may include a medical device, a display device, and a control device. The medical device may be configured to generate a medical image sequence of a subject. The display device may be configured to display the medical image sequence. The control device may be configured to control a display of the medical image sequence on the display device. The control device may include a touch control panel. The touch control panel may include a plurality of predetermined regions corresponding to a plurality of gesture instructions. The control device may be configured to receive a target gesture instruction with respect to a target predetermined region among the plurality of predetermined regions. In response to the target gesture instruction, the control device may be configured to generate a control signal for controlling the display device to perform a target operation on the medical image sequence based on a corresponding relationship between the plurality of gesture instructions and a plurality of operations of the display device.

According to yet another aspect of the present disclosure, a method for controlling a display of a medical image sequence on a display device may be provided. The method may be implemented on a control device. The control device may include a touch control panel, and the touch control panel may include a plurality of predetermined regions corresponding to a plurality of gesture instructions. The method may include receiving a target gesture instruction with respect to a target predetermined region among the plurality of predetermined regions. In response to the target gesture instruction, the method may include generating a control signal for controlling the display device to perform a target operation on the medical image sequence based on a corresponding relationship between the plurality of gesture instructions and a plurality of operations of the display device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
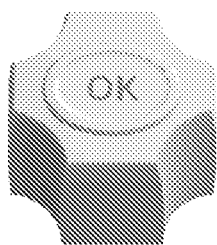
FIG. 1 shows a conventional control device for controlling a display of a medical image sequence.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

An anatomical structure shown in an image of a subject (e.g., a patient) may correspond to an actual anatomical structure existing in or on the subject's body. The term "object" and "subject" in the present disclosure are used interchangeably to refer to a biological object (e.g., a patient, an animal) or a non-biological object (e.g., a phantom). In some embodiments, the object may include a specific part, organ, and/or tissue of the object. For example, the object may include the head, the bladder, the brain, the neck, the torso, a shoulder, an arm, the thorax, the heart, the stomach, a blood vessel, soft tissue, a knee, a foot, or the like, or any combination thereof, of a patient.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Conventionally, a control device includes many operating components to control a display of a medical image sequence on a display device, and each operating component of the control device responds to a relatively small number of operating instructions. Therefore, the use of the conventional control device is relatively complicated, and when a user uses the conventional control device to control the display of the medical image sequence, the user needs to perform complex operations on the conventional control device, thereby resulting in low operation efficiency.

For example, FIG. 1 shows a conventional control device 100 for controlling a display of a medical image sequence. As shown in FIG. 1, the control device 100 includes a control wheel. A press operation on the control wheel may cause the medical image sequence to be displayed to stop the display of the medical image sequence. A toggling operation on the control wheel to the left or right may cause images in the medical image sequence to be switched. A toggling operation on the control wheel up or down may cause the medical image sequence to be switched to display another medical image sequence. A rotating operation on the control wheel may cause reference images to be switched. The control wheel cannot be used to control a cursor, therefore another control element is needed for controlling the cursor. The display of the medical image sequence is controlled by complex mechanical movement of many operating components of the control wheel, therefore the use of the control wheel is very complicated. Moreover, the control wheel has a high failure rate and a large movement resistance, resulting in high cost and a large burden on fingers of a user who operates for a long time.

Some other control devices are provided with many buttons and a turntable. The turntable is configured to control the switch of images in a medical image sequence, and the buttons are configured to realize other functions. A user needs to take a lot of time to learn how to use the control devices. Moreover, when the control device is used to control a display of a medical image sequence, the user needs to observe both the control device and a display device for displaying the medical image sequence, which easily increases the fatigue of the user.

As aspect of the present disclosure provides a control device used for controlling a display of a medical image sequence on a display device. The control device may include a touch control panel. The touch control panel may include a plurality of predetermined regions corresponding to a plurality of gesture instructions. The control device may be configured to receive a target gesture instruction with respect to a target predetermined region among the plurality of predetermined regions. In response to the target gesture instruction, the control device may generate a control signal for controlling the display device to perform a target operation on the medical image sequence based on a corresponding relationship between the plurality of gesture instructions and a plurality of operations of the display device. Compared with the conventional control devices, the control device of the present disclosure may control the display of the medical image sequence via the touch control panel, and the touch control panel includes relatively fewer operating components, the use of the control device is relatively simple and the operation efficiency of a user that operates the control device is relatively high.

Figure 2:
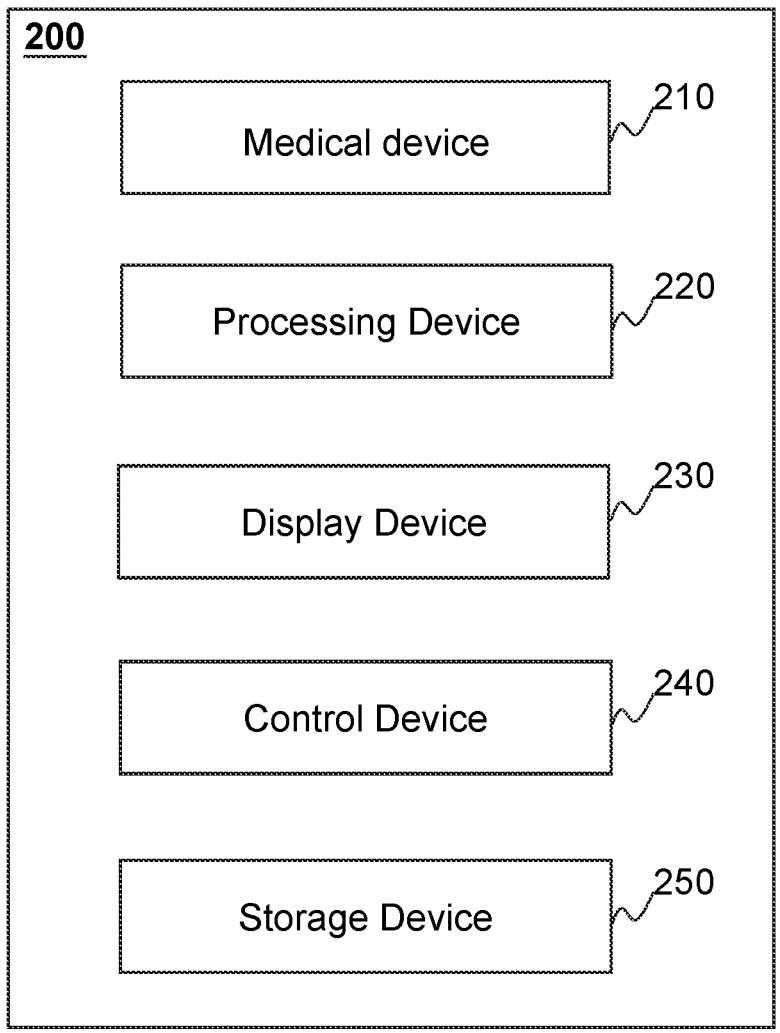
FIG. 2 is a schematic diagram illustrating an exemplary medical system according to some embodiments of the present disclosure.

FIG. 2 is a schematic diagram illustrating an exemplary medical system 200 according to some embodiments of the present disclosure. In some embodiments, as illustrated in FIG. 2, the media system 200 may include a medical device 210, a processing device 220, a display device 230, a control device 240, and a storage device 250. The components of the medical system 200 may be connected in various manners.

The medical device 210 may be an imaging device for generating or provide image data related to a subject via scanning the subject. In some embodiments, the subject may include a biological subject and/or a non-biological subject. For example, the subject may include a specific portion of a body, such as a heart, a breast, or the like. In some embodiments, the medical device 210 may include a single-modality imaging device and/or multi-modality imaging device. The single-modality imaging device may include, for example, a digital subtraction angiography (DSA) device, an ultrasound imaging device, an X-ray imaging device, an computed tomography (CT) device, a magnetic resonance imaging (MRI) device, an ultrasonography imaging device, a positron emission tomography (PET) device, an optical coherence tomography (OCT) imaging device, an ultrasound (US) imaging device, an intravascular ultrasound (IVUS) imaging device, a near-infrared spectroscopy (NIRS) imaging device, a far-infrared (FIR) imaging device, or the like, or any combination thereof. The multi-modality imaging device may include, for example, an X-ray imaging-magnetic resonance imaging (X-ray-MRI) device, a positron emission tomography-X-ray imaging (PET-X-ray) device, a single-photon emission computed tomography-magnetic resonance imaging (SPECT-MRI) device, a positron emission tomography-computed tomography (PET-CT) device, a C-arm system, a digital subtraction angiography-magnetic resonance imaging (DSA-MRI) device, etc. In some embodiments, the medical device 210 may include an image-guided radiation therapy (IGRT) device, such as a CT-linac device, or the like. It should be noted that the imaging device described below is merely provided for illustration purposes, and not intended to limit the scope of the present disclosure.

The processing device 220 may process data and/or information obtained from components (e.g., the medical device 210, the control device 240, the storage device 250) of the medical system 200. For example, the processing device 220 may reconstruct one or more images of the subject based on the image data collected by the medical device 210. In some embodiments, the processing device 220 may reconstruct a plurality of images based on image data generated during a scan of the subject. The plurality of images may be arranged sequentially (e.g., in time) to form a medical image sequence.

In some embodiments, the processing device 220 may be a single server or a server group. The server group may be centralized or distributed. In some embodiments, the processing device 220 may be local or remote. Merely for illustration, only one processing device 220 is described in the medical system 200. However, it should be noted that the medical system 200 in the present disclosure may also include multiple processing devices. Thus operations and/or method steps that are performed by one processing device 220 as described in the present disclosure may also be jointly or separately performed by the multiple processing devices. For example, if in the present disclosure the processing device 220 of the medical system 200 executes both process A and process B, it should be understood that the process A and the process B may also be performed by two or more different processing devices jointly or separately in the medical system 200 (e.g., a first processing device executes process A and a second processing device executes process B, or the first and second processing devices jointly execute processes A and B).

In some embodiments, the processing device 220 may include one or more modules configured to perform the methods of the present disclosure (e.g., process 900). For example, the processing device 220 may include an acquisition module, a determination module, and an adjustment module. For illustration purposes, the implementation of the process 900 is described hereinafter. The acquisition module may be configured to obtain information relating to the medical system 200. For example, the acquisition module may obtain a medical image sequence that needs to be displayed on the display device 230. The determination module may be configured to determine an initial play speed and an adjustment value of the medical image sequence. The adjustment module may be configured to adjust the initial play speed of the medical image sequence based on the adjustment value. More descriptions regarding the process 900 may be found elsewhere in the present disclosure (e.g., FIG. 9 and the descriptions thereof).

The display device 230 may be configured to display information received from other components of the medical system 200. For example, the display device 230 may display one or more medical image sequences received from the processing device 220 to a user (e.g., a doctor). The display device 230 may include a liquid crystal display (LCD), a light emitting diode (LED)-based display, a flat panel display or curved screen (or television), a cathode ray tube (CRT), a virtual reality device, an augmented reality device, or the like, or a combination thereof.

The control device 240 may be used for controlling a display of a medical image sequence on the display device 230. The medical image sequence may include a plurality of images. For example, the control device 240 may control the display device 230 to perform one or more target operations. Exemplary target operations may include switching images in the medical image sequence, switching the medical image sequence to display another medical image sequence, moving a cursor on the display device, displaying the medical image sequence, stopping displaying the medical image sequence, choosing an image in the medical image sequence, changing a switching manner of images in the medical image sequence, or the like, or any combination thereof.

In some embodiments, the control device 240 may include a touch control panel. The touch control panel may include a plurality of predetermined regions corresponding to a plurality of gesture instructions. The control device 240 may be configured to receive a target gesture instruction with respect to a target predetermined region among the plurality of predetermined regions. In response to the target gesture instruction, the control device 240 may generate a control signal for controlling the display device 230 to perform a target operation on the medical image sequence based on a corresponding relationship between the plurality of gesture instructions and a plurality of operations of the display device 230. More descriptions regarding the control device 240 may be found elsewhere in the present disclosure (e.g., FIG. 3A and the descriptions thereof).

The storage device 250 may store data, instructions, and/or any other information. In some embodiments, the storage device 250 may store data obtained from components (e.g., the medical device 210, the processing device 220, the display device 230, the control device 240, etc.) of the medical system 200. For example, the storage device 250 may store scan data collected by the medical device 210. As another example, the storage device 250 may store one or more image sequences of the subject displayed on the display device 230. As still another example, the storage device 250 may store the corresponding relationship between the plurality of gesture instructions and the plurality of operations of the display device 230. In some embodiments, the storage device 250 may store data and/or instructions that the processing device 220 may execute or use to perform exemplary methods described in the present disclosure.

It should be noted that the above description of the medical system 200 is merely provided for the purposes of illustration, and not intended to limit the scope of the present disclosure. For persons having ordinary skills in the art, multiple variations and modifications may be made under the teachings of the present disclosure. For example, the medical system 200 may include one or more additional components and/or one or more components of the medical system 200 described above may be omitted. Additionally or alternatively, two or more components of the medical system 200 may be integrated into a single component. For example, the processing device 220 may be integrated into the control device 240. A component of the medical system 200 may be implemented on two or more sub-components.

Figure 3A:
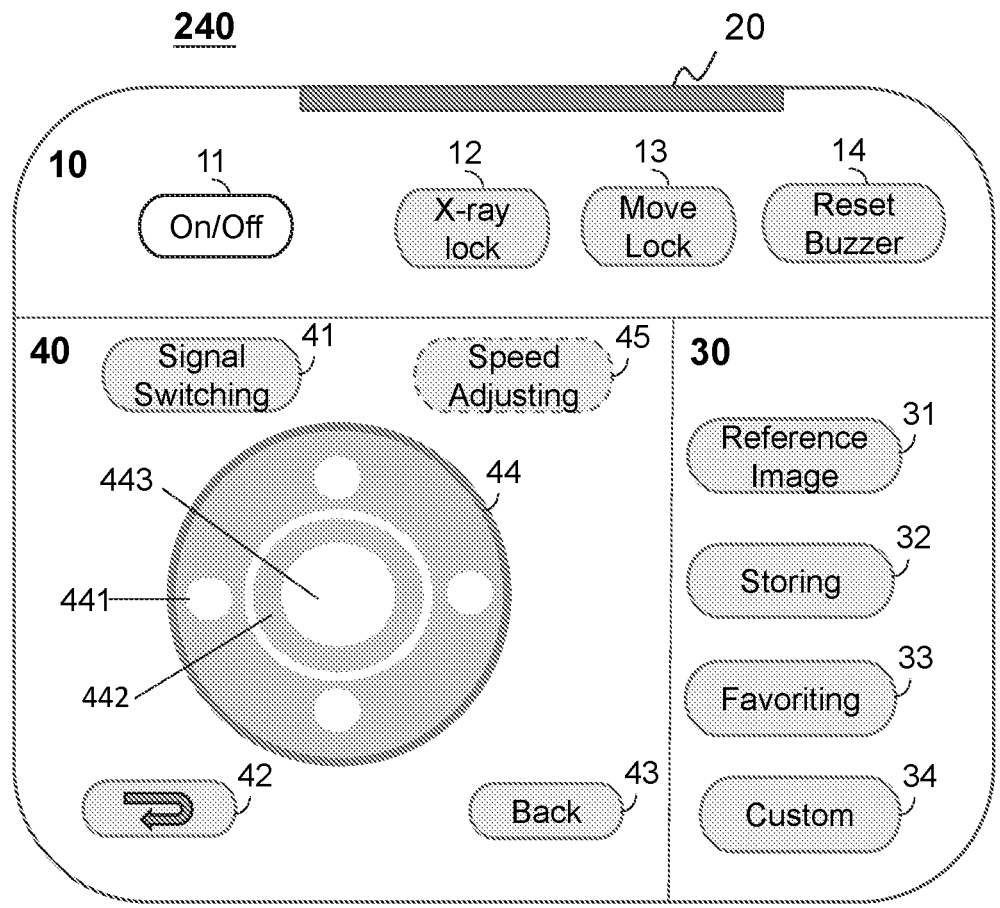
FIG. 3A is a schematic diagram illustrating an exemplary control device according to some embodiments of the present disclosure.

FIG. 3A is a schematic diagram illustrating an exemplary control device 240 according to some embodiments of the present disclosure.

As shown in FIG. 3A, the control device 240 may include a general functional area 10, an indicator light 20, a storage and favoriting region 30, and a display control region 40.

The general functional region 10 may include a switch element 11, an X-ray lock element 12, a move lock element 13, a reset buzzer element 14, or the like, or any combination thereof. The switch element 11 may be configured to turn the control device 240 on or off. The ray lock element 12 may be configured to control emitting of X-rays of the medical device 210. The move lock element 13 may be configured to control movements of one or more components of the medical device 210. The reset buzzer element 14 may be configured to generate an alarm to remind that an operation of the media system 200 exceeds preset requirements, for example, continuous emission of X-rays exceeds a preset time, and when the reset buzzer element 14 is pressed, the alarm is cancelled.

The indicator light 20 may be configured to indicate whether a scan is in progress. For example, when the medical device 210 is scanning a subject, the indicator light 20 may emit light (e.g., light with specific color) to indicate that the scan is in progress, which may remind a user (e.g., a doctor) to stay away from the medical device 210 to avoid danger.

The storage and favoriting region 30 may include a reference image switching element 31, a storing element 32, a favoriting element 33, a custom element 34, or the like, or any combination thereof. The reference image switching element 31 may be configured to switch reference images displayed on the display device 230. The storage element 32 may be configured to store one or more images in a medical image sequence displayed on the display device 230. The favoriting element 33 may be combination to favorite one or more images in the medical image sequence displayed on the display device 230. The custom element 34 may be configured to perform one or more custom operations relating to storage and favoriting. For example, in a DSA system, the custom element 34 may be configured to perform one or more operations such as switching between a subtraction image sequence and a non-subtraction image sequence, switching to a roadmap mode when a fluoroscopic image acquisition is performed, displaying a patient manage list, etc.

The display control region 40 may include a signal switching element 41, a return element 42, a reverse element 43, a touch control panel 44, or the like, or any combination thereof. The signal switching element 41 may be configured to switch between a live interface displaying real-time images and a review interface displaying historical images, so that the display control region 40 controls different interfaces. The return element 42 may be configured to return to a previous menu. The reverse element 43 may be configured to switch between a loop play mode and a list play mode. The touch control panel 44 may be configured to control a display of a medical image sequence displayed on the display device 230.

In some embodiments, an element in the general functional region 10, the storage and favoriting region 30, and the display control region 40 may include any suitable form such as a touch control button, a protruding mechanical button, etc.

In some embodiments, the touch control panel 44 may include a plurality of predetermined regions corresponding to a plurality of gesture instructions. Each of the plurality of predetermined regions may correspond to one or more of the plurality of gesture instructions.

In some embodiments, the plurality of predetermined regions may include a direction adjustment region 441, a quick browse region 442, and a determination region 443. In some embodiments, a shape and a position of a predetermined region may be set according to actual needs. For example, the quick browse region 442 may be located between the direction adjustment region 441 and the determination region 443. The quick browse region 442 may be a ring region around the determination region 443. The determination region 443 may have a shape such as a square, a circle, a triangle, etc. The direction adjustment region 441 may include four sub-regions evenly spaced outside the quick browse region 442. In some embodiments, the shapes of the four sub-regions may be the same or different. Each of the four sub-regions may have a shape such as a square, a circle, a triangle, etc.

Figure 3B:
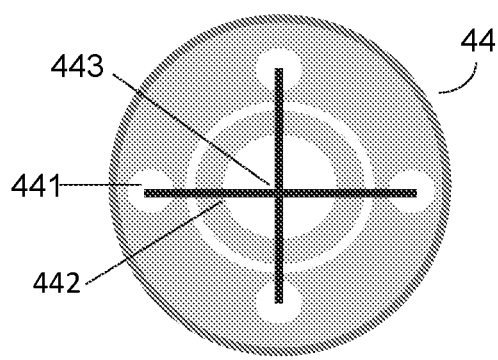
FIG. 3B is a schematic diagram illustrating an exemplary touch control panel according to some embodiments of the present disclosure.

Merely by way of example, FIG. 3B is a schematic diagram illustrating an exemplary touch control panel 44 according to some embodiments of the present disclosure. As shown in FIG. 3B, the four sub-regions of the direction adjustment region 441 are evenly distributed at four endpoints of a "+" shaped pattern. The determination region 443 is arranged at an intersection of the "+" shaped pattern. The quick browse region 442 is a ring region located between the intersection and the four endpoints of the "+" shaped pattern. A horizontal line and a vertical line of the "+" shaped pattern may be vertical or substantially vertical (e.g., an angle between the horizontal line and the vertical line of the "|" shaped pattern is between 85° and 95°).

In some embodiments, the control device 240 may be configured to receive a target gesture instruction with respect to a target predetermined region among the plurality of predetermined regions. Exemplary target gesture instructions may include a press operation, a sliding operation, or the like.

In response to the target gesture instruction, the control device 240 may generate a control signal for controlling the display device 230 to perform a target operation on the medical image sequence based on a corresponding relationship between the plurality of gesture instructions and a plurality of operations of the display device. Exemplary target operations may include switching images in the medical image sequence, switching the medical image sequence to display another medical image sequence, moving a cursor on the display device, displaying the medical image sequence, stopping displaying the medical image sequence, choosing an image in the medical image sequence, changing a switching manner of images in the medical image sequence, adjusting an initial play speed of the medical image sequence, or the like, or any combination thereof.

In some embodiments, the corresponding relationship between the plurality of gesture instructions and the plurality of operations of the display device may be set manually by a user or a default setting of the medical system 200. For example, a user may set that a clockwise sliding operation on the quick browse region 442 corresponds to switching images forwardly, and a counterclockwise sliding operation on the quick browse region 442 corresponds to switching images backwardly according to a habit of the user. In some embodiments, the corresponding relationship between the plurality of gesture instructions and the plurality of operations of the display device may be previously generated and stored in a storage device (e.g., the storage device 250 or an external device). The control device 240 may obtain the corresponding relationship, and determine the target operation according to the target gesture instruction and the corresponding relationship. Then, the control device 240 may generate the control signal for controlling the display device 230 to perform the target operation on the medical image sequence.

In some embodiments, the target predetermined region may be the direction adjustment region 441, the target gesture instruction may include a press operation on the direction adjustment region 441, and the target operation may include at least one of switching images in the medical image sequence, switching the medical image sequence to display another medical image sequence, or moving a cursor on the display device. As used herein, a press operation may include a short press operation (also referred to as a click operation) or a long press operation. If a duration of a press operation is smaller than a press threshold, the press operation may be referred to a short press operation. If a duration of a press operation is not smaller than the press threshold, the press operation may be referred to a long press operation.

Figure 4:
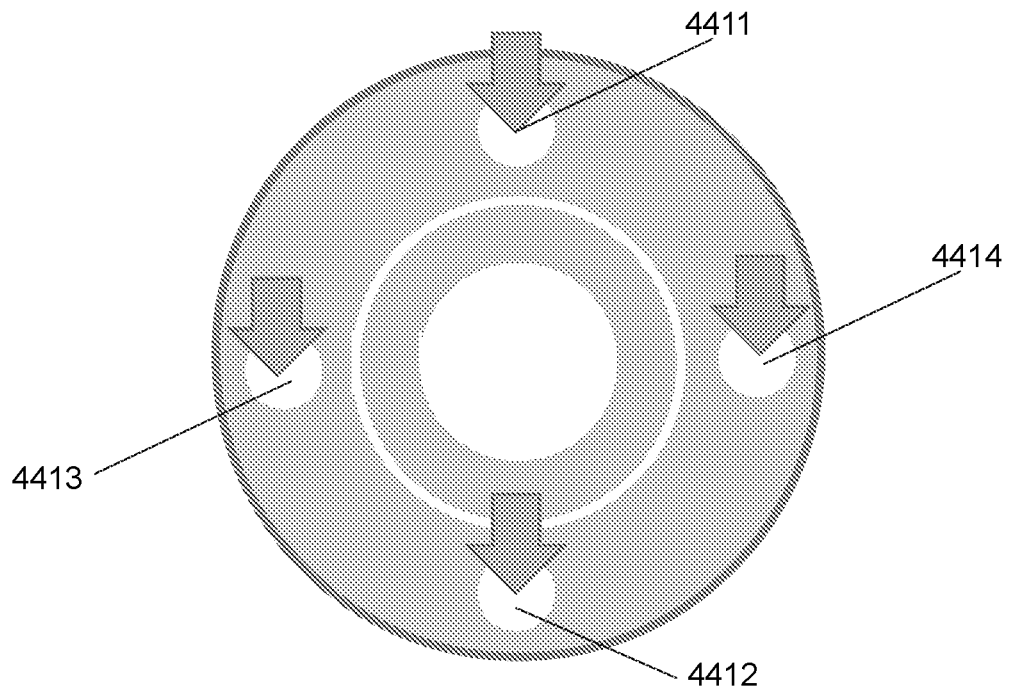
FIG. 4 is a schematic diagram illustrating exemplary press operations on a direction adjustment region according to some embodiments of the present disclosure.

For example, FIG. 4 is a schematic diagram illustrating exemplary press operations on a direction adjustment region according to some embodiments of the present disclosure. As shown in FIG. 4, the direction adjustment region 411 includes fourth sub-regions 4411, 4412, 4413, and 4414, and grey arrows represent press operations on the sub-regions 4411, 4412, 4413, and 4414. If the target gesture instruction is a click operation on the sub-region 4411 when the medical image sequence is displaying on the display device 230, the target operation may be switching the medical image sequence to display a previous medical image sequence; if the target gesture instruction is a click operation on the sub-region 4411 when the medical image sequence is not displaying on the display device 230, the target operation may be moving the cursor up on the display device 230 by a preset distance. As used herein, that the medical image sequence is displaying on the display device 230 may refer to switching and displaying the images in the medical image sequence in an order. If the target gesture instruction is a long press operation on the sub-region 4411 when the medical image sequence is displaying on the display device 230, the target operation may be continuously switching the current medical image sequence displayed on the display device 230 to previous medical image sequences; if the target gesture instruction is a long press operation on the sub-region 4411 when the medical image sequence is not displaying on the display device 230, the target operation may be continuously moving the cursor up on the display device 230.

If the target gesture instruction is a click operation on the sub-region 4412 when the medical image sequence is displaying on the display device 230, the target operation may be switching the medical image sequence to display a next medical image sequence; if the target gesture instruction is a click operation on the sub-region 4412 when the medical image sequence is not displaying on the display device 230, the target operation may be moving the cursor down on the display device 230 by a preset distance. If the target gesture instruction is a long press operation on the sub-region 4412 when the medical image sequence is displaying on the display device 230, the target operation may be continuously switching the current medical image sequences displayed on the display device 230 to next medical image sequences; if the target gesture instruction is a long press operation on the sub-region 4412 when the medical image sequence is not displaying on the display device 230, the target operation may be continuously moving a cursor down on the display device 230.

If the target gesture instruction is a click operation on the sub-region 4413 when the medical image sequence is displaying on the display device 230, the target operation may be switching the current image in the medical image sequence displayed on the display device 230 to display a previous image in the medical image sequence; if the target gesture instruction is a click operation on the sub-region 4413 when the medical image sequence is not displaying on the display device 230, the target operation may be moving a cursor left on the display device 230 by a preset distance. If the target gesture instruction is a long press operation on the sub-region 4413 when the medical image sequence is displaying on the display device 230, the target operation may be continuously switching the current image displayed on the display device 230 to previous images in the medical image sequence; if the target gesture instruction is a long press operation on the sub-region 4413 when the medical image sequence is not displaying on the display device 230, the target operation may be continuously moving the cursor left on the display device 230.

If the target gesture instruction is a click operation on the sub-region 4414 when the medical image sequence is displaying on the display device 230, the target operation may be switching the current image displayed on the display device 230 to next images o in the medical image sequence; if the target gesture instruction is a click operation on the sub-region 4414 when the medical image sequence is not displaying on the display device 230, the target operation may be moving the cursor right once on the display device 230 by a preset distance. If the target gesture instruction is a long press operation on the sub-region 4414 when the medical image sequence is displaying on the display device 230, the target operation may be continuously switching the current image displayed on the display device 230 to next images in the medical image sequence; if the target gesture instruction is a long press operation on the sub-region 4414 the medical image sequence is not displaying on the display device 230, the target operation may be continuously moving a cursor right on the display device 230.

In some embodiments, when the medical image sequence is displaying on the display device 230 and the medical image sequence is the first medical image sequence among a plurality of medical image sequences to be displayed, the press operation (e.g., the click operation or the long press operation) on the sub-region 4411 may include stopping switching, or switching the medical image sequence to the final medical image sequence among the medical image sequences. In some embodiments, when the medical image sequence is displaying on the display device 230 and the medical image sequence is the final medical image sequence, the press operation on the sub-region 4412 may include stopping switching, or switching the medical image sequence to the first medical image sequence. In some embodiments, when the medical image sequence is displaying on the display device 230 and the current image displayed on the display device 230 is the first image among the images in the medical image sequence, the press operation on the sub-region 4413 may include stopping switching, or switching the current image to the final image among the medical image sequence. In some embodiments, when the medical image sequence is displaying on the display device 230 and the current image displayed on the display device 230 is the final image, the press operation on the sub-region 4414 may include stopping switching, or switching the current image to the first image. In some embodiments, when the cursor is moved to an edge of a screen of the display device 230, the press operation may include stopping moving or moving the cursor to another edge opposite to the edge.

In some embodiments, the target predetermined region may be the quick browse region 442, the target gesture instruction may include a sliding operation on the quick browse region 442, and the target operation may include changing a switching manner of images in the medical image sequence. The sliding operation may include a clockwise sliding operation, a counterclockwise sliding operation, etc. The changing the switching manner of images may include switching images forwardly or switching images backwardly.

Figure 5:
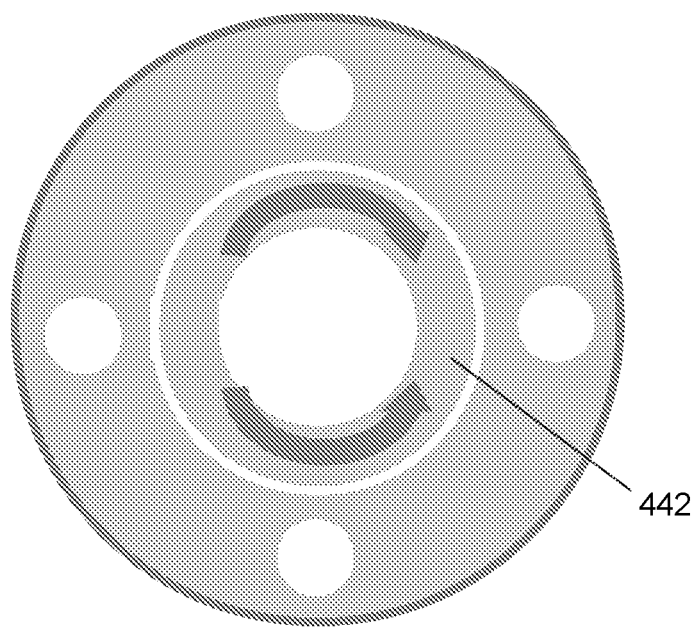
FIG. 5 is a schematic diagram illustrating exemplary sliding operations on a quick browse region according to some embodiments of the present disclosure.

For example, FIG. 5 is a schematic diagram illustrating exemplary sliding operations on a quick browse region according to some embodiments of the present disclosure. As shown in FIG. 5, a gray clockwise arrow represents a clockwise sliding operation on the quick browse region 442, and a gray counterclockwise arrow represents a counterclockwise sliding operation on the quick browse region 442. If the target gesture instruction is the clockwise sliding operation on the quick browse region 442 when the medical image sequence is displaying on the display device 230, the target operation may be switching images in the medical image sequence forwardly (e.g., from the first image to the final image in the medical image sequence); if the target gesture instruction is the counterclockwise sliding operation on the quick browse region 442 when the medical image sequence is displaying on the display device 230, the target operation may be switching images in the medical image sequence backwardly (e.g., from the final image to the first image in the medical image sequence).

In some embodiments, the switching images forwardly or switching images backwardly may be performed based on a sliding speed or a sliding displacement of the sliding operation. For example, the higher the sliding speed, the faster the speed of the switching of the images. As another example, a count of images that are switched may be proportional to the sliding displacement of the sliding operation. Merely by way of example, if the medical image sequence has 360 images and the current image displayed on the display device 230 is the first image, when a clockwise sliding operation of 180° is performed on the quick browse region 442, the medical image sequence may be switched to the $180^{th}$ image in the medical image sequence; if the current image displayed on the display device 230 is the $180^{th}$ image, when a counterclockwise sliding operation of 90° is performed on the quick browse region 442, the medical image sequence may be switched to the $90^{th}$ image in the medical image sequence. In this way, a user may quickly determine a target image in the medical image sequence, thereby improving the efficiency of the disease diagnosis or treatment.

Figure 6:
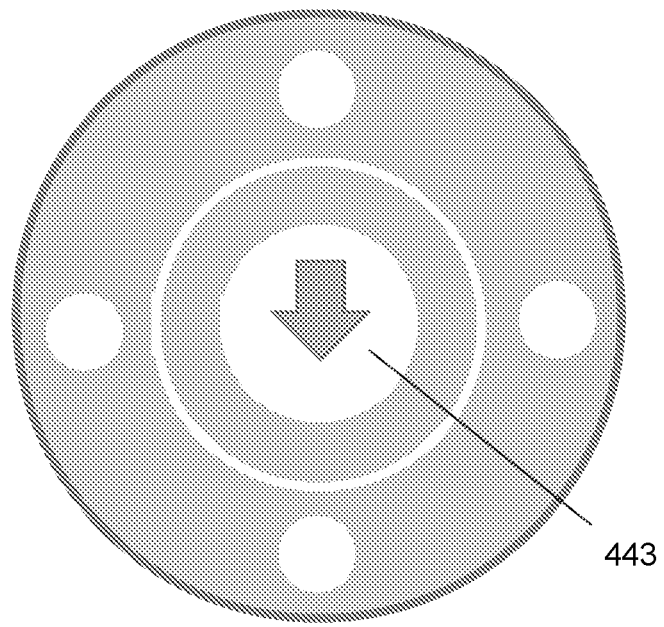
FIG. 6 is a schematic diagram illustrating an exemplary press operation on a determination region according to some embodiments of the present disclosure.

In some embodiments, the target predetermined region may be the determination region, the target gesture instruction may include a press operation on the determination region, and the target operation may include at least one of displaying the medical image sequence, stopping displaying the medical image sequence, or choosing an image in the medical image sequence. For example, FIG. 6 is a schematic diagram illustrating an exemplary press operation on a determination region according to some embodiments of the present disclosure. As shown in FIG. 6, a grey arrow represents a press operation on the determination region 443. When the medical image sequence is displaying on the display device 230, the target operation may be stopping displaying the medical image sequence; when the medical image sequence is not displaying on the display device 230, the target operation may be displaying the medical image sequence; when an image of the medical image sequence is selected, the target operation may be confirming the selection of the specific image.

Figure 7:
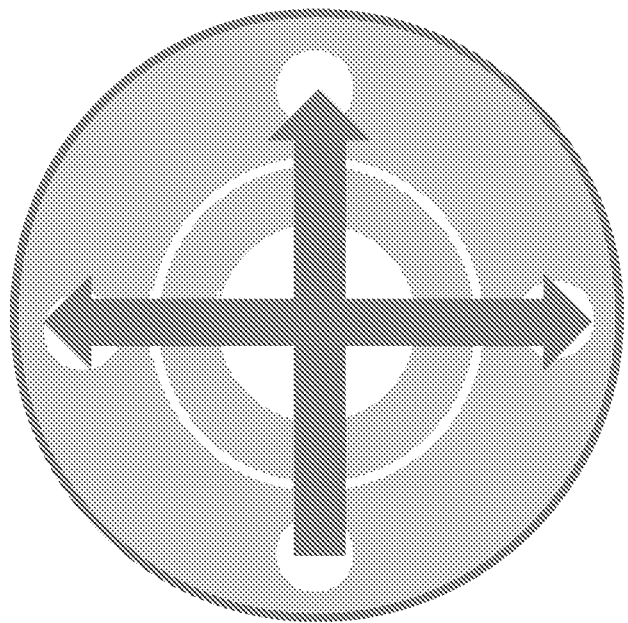
FIG. 7 is a schematic diagram illustrating an exemplary single direction sliding operation and an exemplary dual direction sliding operation on the touch control panel 44 according to some embodiments of the present disclosure.

In some embodiments, the target predetermined region may be any region of the touch control panel 44, the target gesture instruction may include a single direction sliding operation on the region or a dual direction sliding operation on the region. The single direction sliding operation refers to sliding towards one direction. When the target gesture instruction is the single direction sliding operation, the target operation may include moving a portion of an image displayed on the display device 230. The dual direction sliding operation refers to sliding towards two directions. When the target gesture instruction is the dual direction sliding operation, the target operation may include enlarging an image displayed on the display device 230, or shrinking an image displayed on the display device 230. For example, FIG. 7 is a schematic diagram illustrating an exemplary single direction sliding operation and an exemplary dual direction sliding operation on the touch control panel 44 according to some embodiments of the present disclosure. As shown in FIG. 7, a grey single direction arrow represents a single direction sliding operation on the touch control panel 44, and a grey dual direction arrow represents a dual direction sliding operation on the touch control panel 44. When the target gesture instruction is the single direction sliding operation, the target operation may include moving a portion of an image displayed on the display device 230. When the target gesture instruction is the dual direction sliding operation on the region, the target operation may include enlarging an image displayed on the display device 230.

In some embodiments, images in the medical image sequence may be displayed on the display device 230 with an initial play speed. As used herein, a play speed of a medical image sequence may relate to a switching frequency of images in the medical image sequence. For example, if the play speed of the medical image sequence is 5 images per minute, it indicates that 5 images are switched every minute. The lager the play speed is, the more images may be switched per minute. The initial play speed may be a play speed that has not been adjusted by a user. The target operation may include adjusting the initial play speed of the medical image sequence. In some embodiments, the initial play speed may be set manually by a user (e.g., a doctor), a default setting of the medical system 200, or determined automatically by the processing device 220. In some embodiments, the initial play speed may be determined based at least in part on feature information of the medical image sequence. More descriptions regarding the determination of the initial play speed may be found elsewhere in the present disclosure. See, e.g., operation 920 in FIG. 9 and relevant descriptions thereof.

In some embodiments, the control device 240 may further include a speed adjusting element 45. The speed adjusting element 45 may be configured to determine an adjustment value of the initial play speed. As used herein, the adjustment value of the initial play speed refers to an amount by which the initial display speed needs to be adjusted (i.e., increased or decreased).

In some embodiments, the adjustment value may be set manually by a user (e.g., a doctor), a default setting of the medical system 200, or determined automatically by the processing device 220. For example, the target gesture instruction may include a press operation on the speed adjustment element 45. The adjustment value may be determined based on the press operation on the speed adjusting element 45. More descriptions regarding the determination of the adjustment value may be found elsewhere in the present disclosure. See, e.g., operation 930 in FIG. 9 and relevant descriptions thereof.

In some embodiments, the speed adjusting element 45 may be of any suitable form, such as a touch control button, a protruding mechanical button, etc. Merely by way of example, the speed adjusting element 45 may be one of the plurality of predetermined regions on the touch control panel 44.

In some embodiments, the speed adjusting element 45 may include a pressure sensor, and the adjustment value may be determined based on a pressure exerted on the pressure sensor by the press operation. For example, the larger the pressure is, the adjustment value may be larger.

In some embodiments, the control device 240 may further include an identification component configured to collect identity information of a user that operates the control device 240. The identification component may include an image recognition component (e.g., a camera), a fingerprint recognition component, a voiceprint recognition component (e.g., a microphone), or the like, or any combination thereof. The identify information may include facial information, fingerprint information, voice information, and/or any information that can be used to determine the identify of the user. For example, the image recognition component may collect the identity information of the user by performing a face recognition on the user. Further, the initial play speed or the corresponding relationship between the plurality of gesture instructions and the plurality of operations of the display device may be determined based on the identity information of the user. In this way, the control device 240 may adapt to operating habits of different users, thereby improving usability of the control device 240.

As described in elsewhere of the present disclosure, conventional control devices include many operating components to control a display of a medical image sequence on a display device since a single operating component of the control device responds to a relatively small number of operating instructions. Therefore, the use of the conventional control device is relatively complicated, and when a user uses the conventional control device to control the display of the medical image sequence, the user needs to perform complex operations on the conventional control device, thereby resulting in low operation efficiency. Compared with the conventional control devices, the control device of the present disclosure may control the display of the medical image sequence via the touch control panel, and the touch control panel only includes relatively few operating components, the use of the control device is relatively simple and the operation efficiency of a user that operates the control device is relatively high.

It should be noted that the above description of the control device 240 is merely provided for the purposes of illustration, and not intended to limit the scope of the present disclosure. For persons having ordinary skills in the art, multiple variations and modifications may be made under the teachings of the present disclosure. For example, the control device 240 may include one or more additional components/elements and/or one or more components/elements of the control device 240 described above may be omitted. Additionally or alternatively, two or more components/elements of the control device 240 may be integrated into a single component. A component/element of the control device 240 may be implemented on two or more sub-components/sub-element. In addition, the position, the shape, and/or the size of a component of the control device 240 can be adjusted according to an actual need.

Figure 9:
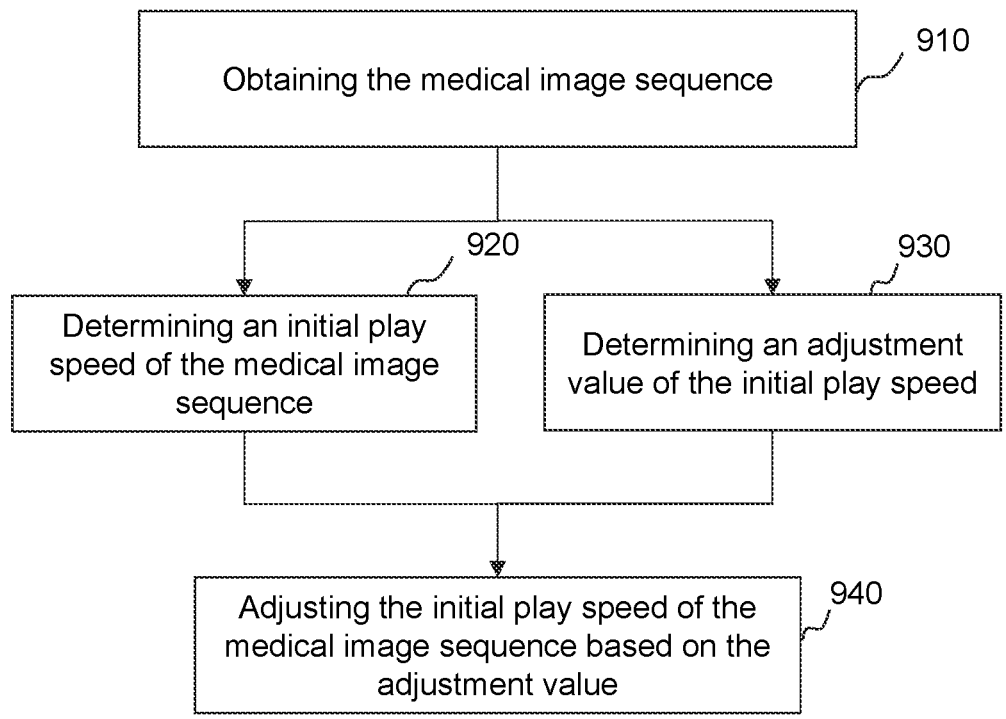
FIG. 9 is a flowchart illustrating an exemplary process for adjusting an initial play speed of a medical image sequence according to some embodiments of the present disclosure.

FIG. 9 is a flowchart illustrating an exemplary process for adjusting an initial play speed of a medical image sequence according to some embodiments of the present disclosure. In some embodiments, process 900 may be executed by the medical system 200. For example, the process 900 may be implemented as a set of instructions (e.g., an application) stored in a storage device (e.g., the storage device 250). In some embodiments, the processing device 220 may execute the set of instructions and may accordingly be directed to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting.

In 910, the processing device 220 may obtain the medical image sequence. In some embodiments, operation 910 may be performed by the acquisition module of the processing device 220.

The medical image sequence may need to be displayed on the display device 230 and be reconstructed based on scan data acquired by scanning a subject with the medical device 210. In some embodiments, as described in FIG. 2, the processing device 220 may reconstruct the medical image sequence based on the scan data. In some embodiments, the medical image sequence may be previously generated and stored in a storage device (e.g., the storage device 250 or an external), and the medical image sequence may be retrieved from the storage device.

In 920, the processing device 220 may determine an initial play speed of the medical image sequence. In some embodiments, operation 920 may be performed by the determination module of the processing device 220.

As described in elsewhere of the present disclosure, a play speed of a medical image sequence may relate to a switching frequency of images in the medical image sequence. The initial play speed may be a play speed that has not been adjusted by a user.

The initial play speed of the medical image sequence may be determined based on a user instruction or a default setting of the medical system 200. Alternatively, the initial play speed may be determined by analyzing information relating to a user that needs to operate the control device 240, information relating to the medical image sequence, information relating to one or more historical medical image sequences, or the like, or any combination thereof.

In some embodiments, initial play speeds corresponding to different users may be previously determined, and stored in a storage device (e.g., the storage device 250 or an external). The processing device 220 may obtain identity information of a user that needs to operate the control device 240. Further, the control device 240 may retrieve the initial play speed corresponding to the user from the storage device based on the identity information of the user. In this way, the initial play speed that matches the user may be quickly determined, which may reduce the time for the user to adjust the initial play speed, thereby improving the operation efficiency of the user.

In some embodiments, the initial play speed may be determined based at least in part on feature information of the medical image sequence. Exemplary feature information of the medical image sequence may include a scan region of the subject, a count of images in the medical image sequence, a type of images (e.g., CT images, MRI images, etc.) in the medical image sequence, or the like, or any combination thereof. For example, if an area of the scan region of the subject is relatively large, the initial play speed may be relatively small. As another example, if the count of images in the medical image sequence is relatively large, the initial play speed may be relatively large. As still another example, different types of images may correspond to different initial play speeds.

For example, the processing device 220 may obtain reference information of one or more historical medical image sequences. The reference information may include feature information and a historical display speed of each of the one or more historical medical image sequences. A historical medical image sequence may refer to a medical image sequence that has been displayed on the display device 230 or another display device, which may be reconstructed based on historical scan data acquired by scanning a reference subject. Exemplary feature information of a historical medical image sequence may include a scan region of a reference subject corresponding to the historical medical image sequence, a count of images in the historical medical image sequence, a type of images in the historical medical image sequence, or the like, or any combination thereof. Further, the processing device 220 may determine the initial play speed based on the reference information of the historical medical image sequences and the feature information of the medical image sequence.

Specifically, the processing device 220 may determine one or more candidate medical image sequences from the one or more historical medical image sequences by comparing the reference information of each historical medical image sequence and the feature information of the medical image sequence. A candidate medical image sequence may have the same feature information as or similar feature information to the medical image sequence. For example, the scan region of each candidate medical image sequence may be the same as that of the medical image sequence. As another example, the scan region and the type of each candidate medical image sequence may be the same as those of the medical image sequence. Further, the processing device 220 may determine the initial display speed based on the historical display speeds of the one or more candidate medical image sequences. For example, the processing device 220 may directly designate the historical display speed of one of the one or more candidate medical image sequences as the initial display speed. As another example, the processing device 220 may designate an average of the historical display speeds of the one or more candidate medical image sequences as the initial display speed.

By determining historical medical image sequences with the same feature information as or similar feature information to the medical image sequence, the determined initial play speed may be relatively accurate, that is, the probability that the initial play speed needs to be adjusted may be greatly reduced, thereby improving the operation efficiency of the user.

As another example, the processing device 220 may determine the initial play speed using a play speed determination model based on the feature information of the medical image sequence. The play speed determination model may be a trained machine learning model for determining a paly speed of a medical image sequence. Merely by way of example, the feature information of the medical image sequence may be input into the play speed determination model, and the play speed determination model may output the initial play speed.

In some embodiments, the processing device 220 may obtain the play speed determination model from one or more components of the medical system 200 (e.g., the storage device 250) or an external source via a network. In some embodiments, the play speed determination model may be generated according to a machine learning algorithm. Merely by way of example, the play speed determination model may be generated via training a preliminary model based on a plurality of training samples. Each training sample may include sample feature information of a sample medical image sequence and a reference display speed of the sample medical image sequence, wherein the reference display speed can be used as a ground truth (also referred to as a label) for model training. In some embodiments, the reference display speed may be a display speed adjusted by a user that browsed the sample medical image sequence. In some embodiments, the reference display speed may be a display speed determined or adjusted by a user that browsed the sample medical image sequence.

Since the play speed determination model may learn the optimal mechanism for play speed determination based on a large amount of data, the initial play speed determined using the play speed determination model may be relatively accurate, that is, the probability that the initial play speed needs to be adjusted may be greatly reduced, thereby improving the operation efficiency of the user.

In 930, the processing device 220 may determine an adjustment value of the initial play speed. In some embodiments, operation 920 may be performed by the determination module of the processing device 220.

As used herein, the adjustment value of the initial play speed refers to an amount by which the initial display speed needs to be adjusted (i.e., increased or decreased).

In some embodiments, the adjustment value of the initial play speed may be determined based on a user instruction. For example, as described in FIG. 3A, the control device 240 may further include a speed adjusting element 45, and the adjustment value may be determined based on a user operation on the speed adjusting element 45. In some embodiments, the target gesture instruction may include a press operation on the speed adjustment element 45. The adjustment value may be determined based on the press operation on the speed adjusting element 45. For example, one pressing operation may correspond to a fixed adjustment value, and the user may press the speed adjusting element 45 multiple times until the adjustment value desired by the user is obtained. As another example, the adjustment value increases with the duration of the press operation, and the user may keep pressing the speed adjusting element 45 until the desired adjustment value is obtained.

Figure 8:
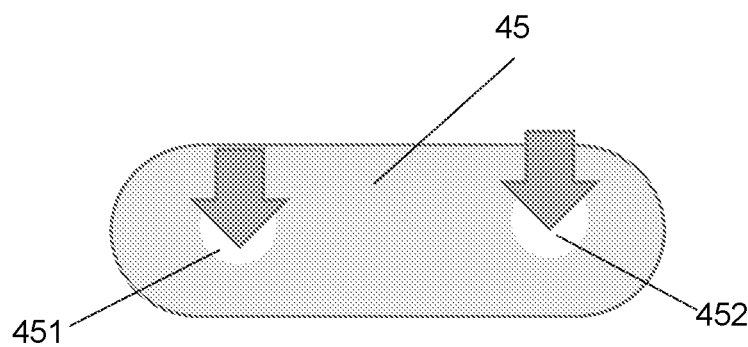
FIG. 8 is a schematic diagram illustrating an exemplary press operation on a speed adjustment element according to some embodiments of the present disclosure.

Merely by way of example, FIG. 8 is a schematic diagram illustrating an exemplary press operation on a speed adjustment element according to some embodiments of the present disclosure. As shown in FIG. 8, grey arrows represent press operations on the speed adjusting element 45. The speed adjusting element 45 includes two members 451 and 452, and grey arrows represent press operations on the members 451 and 452. If the target gesture instruction is a press operation on the member 451, a positive adjustment value may be determined (i.e., the initial play speed may be increased); if the target gesture instruction is a press operation on the member 452, a negative adjustment value may be determined (i.e., the initial play speed may be decreased). The user may press the members 451 and 452 according to needs until the adjustment value desired by the user is obtained.

In some embodiments, the adjustment value of the initial play speed may be determined by the processing device 220 based on one or more historical gesture instructions relating to the initial play speed received by the touch control panel 44 in a preset historical period. Specifically, the processing device 220 may determine a historical adjustment value corresponding to each historical gesture instruction, and determine the adjustment value based on the one or more historical adjustment values corresponding to the one or more historical gesture instructions. For example, if the one or more historical adjustment values gradually increase, that is, each historical adjustment value is greater than the previous historical adjustment value, the processing device 220 may predict that the user wants to continue to increase the adjustment value. At this time, the processing device 220 may adjust the latest historical adjustment value to obtain the current adjustment value. As another example, after the adjustment value is increased, the control device 240 receives an gesture instruction to reduce the current play speed, which indicates that the adjustment value has increased too much, and the processing device 220 may appropriately reduce the adjustment value. In this way, the adjustment value may be automatically determined according to the user's recent operation instructions, thereby improving the efficiency of the determination of the adjustment value.

In some embodiments, the initial play speed and the adjustment value of the initial play speed may be selected from one or more groups of reference speed parameters based at least in part on the feature information of the medical image sequence. Each of the one or more groups of reference speed parameters may include a reference initial play speed and a reference adjustment value. In some embodiments, a group of reference speed parameter may be determined based on displaying records of one or more reference medical image sequences on the display device 230 or another display device. The one or more reference medical image sequences may have the same or similar feature information. For example, an average of one or more initial play speeds and an average of one or more adjustment values of the one or more reference medical image sequences may be designated as the reference initial play speed and the reference adjustment value of the group of reference speed parameter, respectively.

For example, the processing device 220 may determine one or more candidate groups of speed parameters from the one or more groups of speed parameters by comparing the feature information of one or more reference medical image sequences corresponding to each group of speed parameters and the feature information of the medical image sequence. One or more reference medical image sequences corresponding to a candidate group of speed parameters may have the same feature information as or similar feature information to the medical image sequence. For example, the scan regions of the one or more reference medical image sequences corresponding to the candidate group of speed parameters may be the same as that of the medical image sequence. As another example, the scan regions and the types of the one or more reference medical image sequences corresponding to the candidate group of speed parameters may be the same as those of the medical image sequence. Further, the processing device 220 may determine the initial display speed and the adjustment value based on the one or more candidate groups of speed parameters. For example, the processing device 220 may directly designate one group of the one or more candidate groups of speed parameters as the initial display speed and the adjustment value. As another example, the processing device 220 may designate an average of the reference initial display speeds and an average of the reference adjustment values of the one or more candidate groups of speed parameters as the initial display speed and the adjustment value, respectively. In this way, the initial play speed and the adjustment value may be quickly determined and have a relatively large accuracy since the one or more candidate groups of speed parameters may have the same feature information as or similar feature information to the medical image sequence.

In some embodiments, the processing device 220 may determine the initial play speed and the adjustment value using a parameter determination model based on the feature information of the medical image sequence and the identity information of the target user. The parameter determination model may be a trained machine learning model for determining an initial paly speed of a medical image sequence and an adjustment value of the initial paly speed. Merely by way of example, the feature information of the medical image sequence and the identity information of the target user may be input into the parameter determination model, and the parameter determination model may output the initial play speed and the adjustment value.

In some embodiments, the processing device 220 may obtain the parameter determination model from one or more components of the medical system 200 (e.g., the storage device 250) or an external source via a network. In some embodiments, the parameter determination model may be generated according to a machine learning algorithm. Merely by way of example, the parameter determination model may be generated via training a preliminary model based on a plurality of training samples. Each training sample may include sample feature information of a sample medical image sequence, sample identity information of a sample user that browsed the sample image sequence, a reference initial display speed of the sample medical image sequence, and a reference adjustment value of the reference initial display speed, wherein the reference initial display speed and the reference adjustment value can be used as a ground truth (also referred to as a label) for model training. In some embodiments, the reference initial display speed may be an initial display speed of the sample medical image sequence that is not adjusted by the sample user. In some embodiments, the reference adjustment value may be an adjustment value determined by the sample user or an actual adjustment value during the display of the sample medical image sequence.

Since the parameter determination model may learn the optimal mechanism for determining initial play speed and adjustment value based on a large amount of data, the initial play speed and the adjustment value determined using the parameter determination model may be relatively accurate.

In 940, the initial play speed of the medical image sequence may be adjusted based on the adjustment value. In some embodiments, operation 920 may be performed by the adjustment module of the processing device 220.

For example, if the initial play speed needs to be decreased, the adjustment value may be a negative number; if the initial play speed needs to be increased, the adjustment value may be a positive number. A sum of the initial play speed and the adjustment value may be designated as an updated display speed of the medical image sequence.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A control device used for controlling a display of a medical image sequence on a display device, wherein:
   the control device includes a touch control panel,
   the touch control panel includes a plurality of predetermined regions corresponding to a plurality of gesture instructions, wherein the plurality of predetermined regions include a quick browse region, a determination region, and a direction adjustment region, the quick browse region being located between the determination region and the direction adjustment region, the quick browse region being a ring region,
   the control device is configured to:
      receive a target gesture instruction with respect to a target predetermined region among the plurality of predetermined regions;
      in response to the target gesture instruction, generate a control signal for controlling the display device to perform a target operation on the medical image sequence based on a corresponding relationship between the plurality of gesture instructions and a plurality of operations of the display device, wherein the target predetermined region includes the quick browse region, and the target operation includes changing a switching manner of images in the medical image sequence.

2. The control device of claim 1, wherein
   the quick browse region is around the determination region, and
   the direction adjustment region includes four sub-regions evenly spaced outside the quick browse region.

3. The control device of claim 1, wherein
   the target predetermined region includes the direction adjustment region,
   the target gesture instruction includes a press operation on the direction adjustment region, and
   the target operation includes at least one of switching images in the medical image sequence, switching the medical image sequence to display another medical image sequence, or moving a cursor on the display device.

4. The control device of claim 1, wherein
   the target predetermined region includes the determination region, the target gesture instruction includes a press operation on the determination region, and the target operation includes at least one of displaying the medical image sequence, stopping displaying the medical image sequence, or choosing an image in the medical image sequence.

5. The control device of claim 1, wherein
the target gesture instruction includes a sliding operation on the quick browse region.

6. The control device of claim 1, wherein
images in the medical image sequence are displayed on the display device with an initial play speed,
the target operation includes adjusting the initial play speed of the medical image sequence by an adjustment value, and
the initial play speed is determined based at least in part on feature information of the medical image sequence.

7. The control device of claim 6, wherein the control device further includes a speed adjusting element,
the target gesture instruction includes a press operation on the speed adjustment element, and
the adjustment value is determined based on the press operation on the speed adjusting element.

8. The control device of claim 7, wherein the speed adjusting element includes a pressure sensor, and the adjustment value is determined based on a pressure exerted on the pressure sensor by the press operation.

9. The control device of claim 6, wherein the initial play speed and the adjustment value are selected from one or more groups of reference speed parameters each of which includes a reference initial play speed and a reference adjustment value based at least in part on the feature information of the medical image sequence.

10. The control device of claim 6, wherein the adjustment value is determined based on one or more historical gesture instructions received by the touch control panel in a preset historical period.

11. The control device of claim 1, wherein the control device further includes an identification component configured to collect identity information of a user that operates the control device.

12. The control device of claim 5, wherein the sliding operation includes a clockwise sliding operation or a counterclockwise sliding operation.

13. A medical system, comprising:
a medical device, configured to generate a medical image sequence of a subject;
a display device, configured to display the medical image sequence; and
a control device, configured to control a display of the medical image sequence on the display device, wherein:
the control device includes a touch control panel,
the touch control panel includes a plurality of predetermined regions corresponding to a plurality of gesture instructions, wherein the plurality of predetermined regions include a quick browse region, the quick browse region being a ring region,
the control device is configured to:
receive a target gesture instruction with respect to a target predetermined region among the plurality of predetermined regions;
in response to the target gesture instruction, generate a control signal for controlling the display device to perform a target operation on the medical image sequence based on a corresponding relationship between the plurality of gesture instructions and a plurality of operations of the display device, wherein the target predetermined region includes the quick browse region, the target gesture instruction includes a sliding operation on the quick browse region, and the target operation includes changing a switching manner of images in the medical image sequence.

14. A method for controlling a display of a medical image sequence on a display device, the method being implemented on a control device, wherein the control device includes a touch control panel, the touch control panel includes a plurality of predetermined regions corresponding to a plurality of gesture instructions, wherein the plurality of predetermined regions include a quick browse region, the quick browse region being a ring region, and the method comprises:
receiving a target gesture instruction with respect to a target predetermined region among the plurality of predetermined regions; and
in response to the target gesture instruction, generating a control signal for controlling the display device to perform a target operation on the medical image sequence based on a corresponding relationship between the plurality of gesture instructions and a plurality of operations of the display device, wherein the target gesture instruction includes a sliding operation on the quick browse region, the target predetermined region includes the quick browse region, and the target operation includes changing a switching manner of images in the medical image sequence.

15. The method of claim 14, wherein the plurality of predetermined regions further include a determination region and a direction adjustment region, the quick browse region being located between the determination region and the direction adjustment region.

16. The method of claim 15, wherein
the target predetermined region includes the direction adjustment region,
the target gesture instruction includes a press operation on the direction adjustment region, and
the target operation includes at least one of switching images in the medical image sequence, switching the medical image sequence to display another medical image sequence, or moving a cursor on the display device.

17. The method of claim 15, wherein
the target predetermined region includes the determination region,
the target gesture instruction includes a press operation on the determination region, and
the target operation includes at least one of displaying the medical image sequence, stopping displaying the medical image sequence, or choosing an image in the medical image sequence.

18. The method of claim 14, wherein
images in the medical image sequence are displayed on the display device with an initial play speed,
the target operation includes adjusting the initial play speed of the medical image sequence by an adjustment value, and
the initial play speed is determined based at least in part on feature information of the medical image sequence.

* * * * *